(12) United States Patent
Townsend et al.

(10) Patent No.: US 10,744,229 B1
(45) Date of Patent: Aug. 18, 2020

(54) THIOLATED DEVITALIZED TISSUE PARTICLE IMPLANTABLE HYDROGEL

(71) Applicant: The Board of Regents of the University of Oklahoma, Norman, OK (US)

(72) Inventors: Jakob M. Townsend, Norman, OK (US); Michael S. Detamore, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/330,237

(22) PCT Filed: Oct. 25, 2018

(86) PCT No.: PCT/US2018/057515
§ 371 (c)(1),
(2) Date: Mar. 4, 2019

(87) PCT Pub. No.: WO2019/084272
PCT Pub. Date: May 2, 2019

Related U.S. Application Data

(60) Provisional application No. 62/576,947, filed on Oct. 25, 2017.

(51) Int. Cl.
*A61L 27/52* (2006.01)
*A61L 27/20* (2006.01)
*A61L 27/56* (2006.01)

(52) U.S. Cl.
CPC .............. *A61L 27/52* (2013.01); *A61L 27/20* (2013.01); *A61L 27/56* (2013.01); *A61L 2430/02* (2013.01); *A61L 2430/12* (2013.01)

(58) Field of Classification Search
CPC .......... A61L 27/52; A61L 27/20; A61L 27/56; A61L 2430/12; A61L 2430/02
See application file for complete search history.

(56) References Cited

U.S. PATENT DOCUMENTS

| 2009/0017091 A1* | 1/2009 | Daniloff ................ A61L 27/52 424/423 |
| 2016/0235892 A1* | 8/2016 | Detamore ............... A61L 27/54 |
| 2017/0065742 A1* | 3/2017 | Detamore ........... A61L 27/3612 |

FOREIGN PATENT DOCUMENTS

WO  2017143344 A1 * 8/2017

OTHER PUBLICATIONS

International Search Report, dated Jan. 16, 2019, in PCT/US18/57515, filed Oct. 25, 2018.

(Continued)

*Primary Examiner* — Carlos A Azpuru
(74) *Attorney, Agent, or Firm* — Dunlap Codding, P.C.

(57) ABSTRACT

Methods and compositions for use in repairing and/or regenerating tissues are disclosed. A hydrogel precursor composition comprising functionalized tissue particles and functionalized hyaluronic acid that can be deposited into an implant site and converted into a crosslinked hydrogel network which retains the tissue particles at the implant site is disclosed. Also disclosed are methods of forming functionalized tissue particles and functionalized hyaluronic acid for use herein. Kits containing reagents for producing the hydrogel precursor composition are also disclosed, along with methods of producing the hydrogel precursor composition.

46 Claims, 5 Drawing Sheets

(56) References Cited

OTHER PUBLICATIONS

Written Opinion of the International Searching Authority, dated Jan. 16, 2019, in PCT/US18/57515, filed Oct. 25, 2018.
Beck, et al.; "Chondroinductive Hydrogel Pastes Composed of Naturally Derived Devitalized Cartilage," Annals of Biomedical Engineering, (2016), vol. 44, No. 6, pp. 1863-1880.
Townsend, et al.; "Superior Calvarial Bone Regeneration Using Pentenoate-Functionalized Hyaluronic Acid Hydrogels with Devitalized Tendon Particles," Acta Biomaterialia (2018), vol. 71, pp. 148-155.

* cited by examiner

THIOLATED DEVITALIZED TISSUE PARTICLE IMPLANTABLE HYDROGEL

CROSS REFERENCE TO RELATED APPLICATIONS/INCORPORATION BY REFERENCE STATEMENT

The present patent application is a US National Stage Application under 35 USC § 371 of International Application No. PCT/US2018/057515, filed Oct. 25, 2018; which claims priority to U.S. Provisional Patent Application U.S. Ser. No. 62/576,947, filed on Oct. 25, 2017, the entire contents of which are hereby expressly incorporated herein by reference.

BACKGROUND

Traumatic brain injury (TBI) is a life-threatening condition characterized by internal brain swelling, the degree of which can vary greatly. TBI inflicted by a closed head injury or stroke can result in severe brain swelling requiring surgical intervention. The current surgical procedure to treat TBI involves a two-stage surgery. In the first surgery, decompressive craniectomy (DC) is performed in which a large portion of the calvaria is removed to allow un-impeded brain swelling. The portion of calvarial bone removed is considered a critical size defect, as the bone will not naturally heal by itself. After brain swelling has subsided, a second surgery, termed "cranioplasty," is performed to close the cranial vault. The average time between DC and cranioplasty has been reported at 80 days, and during this time, the brain is left un-protected. Syndrome of the trephined (SoT), also known as sinking skin flap syndrome, is a severe neurological condition associated with mood changes, fatigue, dizziness, motor skill problems, and concentration issues. The occurrence of SoT has been connected to patients following DC for the treatment of TBI. The cause of SoT has been attributed to various factors such as changing intracranial pressure or physical distortion of the brain from the weight of the scalp. Immediate relief from SoT has been observed directly after cranioplasty, and it is recommended that cranioplasty be performed as soon as clinically possible to mitigate the occurrence of SoT. The current two-stage surgical treatment is non-advantageous, as it prolongs patient recovery by requiring two separate surgeries and potentially results in the neurological condition SoT.

Various research groups have reported new approaches to treat TBI. In one study, the effect of a single-surgical approach combining DC and autologous bone flap cranioplasty was investigated in a pediatric patient population. High complication rates were found. A potential issue with combining DC and cranioplasty in a single surgical intervention is that current methods, such as autologous bone flap cranioplasty, do not allow the brain to swell, as the constructs are rigid bodies. Most research into TBI treatment has focused on methods to improve brain tissue healing or blocking tissue growth to ease the transition between DC and cranioplasty. Currently available commercial products for calvarial bone regeneration are incapable of being used for cranioplasty following DC, as the treatments are unable to regenerate sufficient bone across the critical size defect. Bone cements offer the ability to harden in place after placement, but do not offer the ability to transition into bone. There is currently an unmet need for a material capable of being implemented in a single-surgery to treat TBI that is capable of remaining flexible during brain swelling, then transitioning to bone after brain swelling has ceased. It is to this unmet need and others described below that the present disclosure is directed.

BRIEF DESCRIPTION OF THE DRAWINGS

Several embodiments of the present disclosure are hereby illustrated in the appended drawings. It is to be noted, however, that the appended drawings only illustrate several embodiments and are therefore not intended to be considered limiting of the scope of the present disclosure.

DETAILED DESCRIPTION

Figure 1:
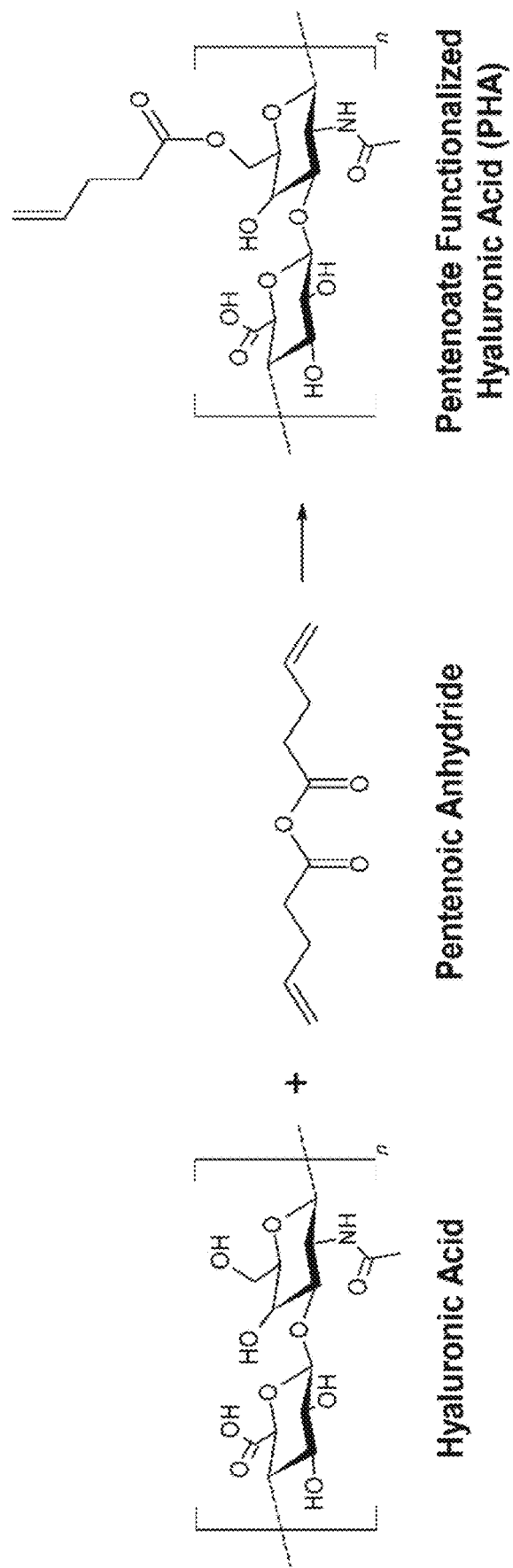
FIG. 1 shows the reaction of hyaluronic acid with 4-pentenoic anhydride to form pentenoate functionalized hyaluronic acid (PHA). In one embodiment of the present disclosure, the PHA can be combined with thiolated tissue particles and crosslinked to form a hydrogel.

In at least certain non-limiting embodiments, the present disclosure is directed to methods of forming functionalized devitalized tissue particles and functionalized hyaluronic acid (functionalized hyaluronan), which can be combined to form a devitalized tissue particle-functionalized hyaluronic acid hydrogel precursor composition. The hydrogel precursor composition can be placed into an implant site such as (but not limited to) a defect site (e.g., a hole, gap, space, void, tear, or the like), then exposed to an activating wavelength, such as (but not limited to) a UV light wavelength, thereby causing crosslinking of the components of the composition to form a crosslinked devitalized tissue particle-hyaluronic acid-based hydrogel composition (crosslinked hydrogel composition or material). The crosslinked hydrogel composition comprises a solidified interconnected polymer network which is retained intact in the implant site, locking the tissue particles in place for retention, and thereby enabling healing and regeneration at the implant site (e.g., bone regeneration). In certain non-limiting embodiments, the hydrogel composition is used for bone regeneration in craniofacial bones such as (but not limited to) the calvarium. In certain non-limiting embodiments, the hydrogel composition is used for cartilage, tendon, and meniscus regeneration and/or repair. In certain non-limiting embodiments, the presently disclosed hydrogel compositions can be used to repair osteochondral defects found in joint disorders, such as (but not limited to) defects in articular cartilage and/or the subchondral bone in joints and joint structures. An implant site of the compositions of the present disclosure may be located in, but is not limited to, a bone, knee, ankle, elbow, shoulder, wrist, hip, vertebra, vertebral disc, patella, femoral head, glenoid of the scapula, growth plate, tendon, ligament, trachea, vocal cord, bronchus, fascia, combinations thereof, and the like. For example (but not by way of limitation), the compositions of the present disclosure may be used to fill gaps or voids between bone or cartilage and an artificial joint component.

The hydrogel precursor compositions of the present disclosure have a paste-like consistency that gives the material excellent handling properties for physical placement, and allowing for user-defined photo-polymerization (crosslinking) for material retention. After the crosslinked hydrogel material solidifies, the incorporated tissue particles and polymer carrier form an interconnected network that retains the tissue particles by covalent linkage. No other available bone-regenerating product is known to have the ability to be solidified in situ in an implant site and retain tissue particles at the implant site.

Before further describing various embodiments of the compositions, kits, and methods of the present disclosure in more detail by way of exemplary description, examples, and results, it is to be understood that the embodiments of the present disclosure are not limited in application to the details of compositions, kits, and methods as set forth in the following description. The embodiments of the compositions, kits, and methods of the present disclosure are capable of being practiced or carried out in various ways not explicitly described herein. As such, the language used herein is intended to be given the broadest possible scope and meaning, and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the compositions, kits, and methods of the present disclosure have been described in terms of particular embodiments, it will be apparent to those of skill in the art that variations may be applied to the compositions, kits, and/or methods described herein, and in the steps or in the sequence of steps of the methods described herein, without departing from the concept, spirit, and scope of the present disclosure. All such similar substitutes and modifications apparent to those having ordinary skill in the art are deemed to be within the spirit and scope of the present disclosure.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein. Non-limiting examples of patents and published patent applications expressly incorporated herein by reference include U.S. Pat. No. 8,715,983 and U.S. Patent Application Publication Nos. 2016/0038643 and 2017/0065742.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the compositions, kits, and methods of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used in this specification and claims, the terms "comprising" (and any form of comprising, such as "comprise" and "comprises"), "having" (and any form of having, such as "have" and "has"), "including" (and any form of including, such as "includes" and "include"), and "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the objects or study subjects. As used herein, the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The terms "about" or "approximately," where used herein when referring to a measurable value such as an amount, percentage, temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. In addition, the use of the terms "one embodiment" and "an embodiment" are not to be construed as limiting in any matter of the scope of the present disclosure.

As used herein, all numerical values or ranges include fractions of the values and integers within such ranges and fractions of the integers within such ranges unless the context clearly indicates otherwise. Thus, to illustrate, reference to a numerical range such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units (for example (but not limited to) where units are Pa) therefore refers to and includes all values or ranges of values of the units, and fractions of the values of the units, and integers within said range, including for example but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of from about 100 units to about 2000 units therefore can be used to set the lower and upper boundaries of a range in accordance with the embodiments of the present disclosure.

The term "pharmaceutically acceptable" refers to compounds and compositions which are suitable for administration to humans and/or animals without undue adverse side effects such as toxicity, irritation, and/or allergic response commensurate with a reasonable benefit/risk ratio.

By "biologically active" is meant the ability of an active agent to modify the physiological system of an organism without reference to how the active agent has its physiological effects.

As used herein, "pure," "substantially pure," or "isolated" means an object species is the predominant species present (i.e., on a molar basis, it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein, the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The terms "subject" and "patient" are used interchangeably herein and will be understood to refer an organism to which the compositions of the present disclosure are applied and used, such as (but not limited to) a vertebrate or more particularly to a warm blooded animal, such as (but not limited to) a mammal or bird. Non-limiting examples of animals within the scope and meaning of this term include dogs, cats, rats, mice, guinea pigs, horses, goats, cattle, sheep, zoo animals, Old and New World monkeys, non-human primates, and humans.

"Treatment" refers to therapeutic treatments, such as (but not limited to) for bone defect healing. The term "treating" refers to administering the composition to a patient for such therapeutic purposes, and may result in an amelioration of the condition or disease.

The terms "therapeutic composition" and "pharmaceutical composition" refer to an active agent composition, such as (but not limited to) the hydrogel precursor and hydrogel compositions described herein, that may be administered to a subject by any method known in the art or otherwise contemplated herein, wherein administration of the composition brings about a therapeutic effect as described elsewhere herein. In addition, certain compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as (but not limited to) toxicity, irritation, and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by a person of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit, or control in the occurrence, frequency, severity, progression, or duration of the condition, or an improvement in a symptom or an underlying cause or a consequence of the condition, or a reversal of the condition. A successful treatment outcome can lead to a "therapeutic effect" or "benefit" of ameliorating, decreasing, reducing, inhibiting, suppressing, limiting, controlling, or preventing the occurrence, frequency, severity, progression, or duration of a condition, or consequences of the condition, in a subject.

A decrease or reduction in worsening, such as (but not limited to) stabilizing the condition, is also a successful treatment outcome. A therapeutic benefit therefore need not be complete ablation or reversal of the condition, or any one, most, or all adverse symptoms, complications, consequences, or underlying causes associated with the condition. Thus, a satisfactory endpoint may be achieved when there is an incremental improvement, such as (but not limited to) a partial decrease, reduction, inhibition, suppression, limit, control, or prevention in the occurrence, frequency, severity, progression, duration, inhibition, or reversal of the condition (e.g., stabilizing), over a short or long duration of time (e.g., seconds, minutes, hours).

The term "hyaluronic acid" or "HA" refers to polymers of repeating disaccharide units composed of D-glucuronic acid and N-acetyl-D-glucosamine, and is also intended to refer to salts of hyaluronic acid.

The term "crosslinked" as used herein refers to an HA molecule with at least one covalent bond that is not found within the repeating disaccharide units of the HA or found between repeating units of the HA molecule, and more particularly refers to covalent linkage of two or more HA molecules via thiolated tissue particles, or to intramolecular covalent linkage via thiolated tissue particles.

The term "hydrogel" as used herein refers to a three-dimensional crosslinked network comprising hyaluronic acid and tissue particles that contains a large amount of water, generally 50 wt % or more. A "hydrogel precursor" is a composition comprising hyaluronic acid and tissue particles that contains a large amount of water and is capable of becoming crosslinked to form a hydrogel.

The term "devitalized" as used herein refers to the substantial decellularization of a tissue (i.e., making a tissue substantially acellular), such that minimal cellular remnants remain. For example, a devitalized tissue is essentially free from reproductively and/or metabolically viable cells.

Returning to discussion of particular embodiments of the present disclosure, the crosslinked hydrogels of the present disclosure form an interconnected network in which the tissue particles therein are covalently bound to a carrier material comprising hyaluronic acid polymer molecules. In addition to the use of the hydrogel material for bone regeneration, the technology can be used for, but is not limited to, autologous chondrocyte implantation using thiolated cartilage, meniscal repair using thiolated meniscus particles, or tendon repair using thiolated tendon particles. Other uses are described elsewhere herein.

Certain non-limiting embodiments of the present disclosure are directed to an implantable hydrogel precursor composition that includes: a devitalized tissue particle composition comprising thiolated devitalized tissue particles; a hyaluronic acid composition comprising functionalized hyaluronic acid molecules; and a photoinitiator for initiating covalent linkage of the functionalized hyaluronic acid molecules to the thiolated devitalized tissue particles. When combined, the devitalized tissue particle composition, the hyaluronic acid composition, and the photoinitiator form a hydrogel precursor composition. In addition, the hydrogel precursor composition is capable of forming a crosslinked hydrogel when exposed to a crosslink-activating wavelength.

Certain non-limiting embodiments of the present disclosure are directed to a kit for use in repair or regeneration of a damaged tissue, wherein the kit includes one or more containers comprising the devitalized tissue particle composition, hyaluronic acid composition, and photoinitiator described herein above or otherwise contemplated herein.

Certain non-limiting embodiments of the present disclosure are directed to a method of forming a hydrogel implant in an implant site in vivo. In the method, a hydrogel precursor composition is formed by combining the devitalized tissue particle composition, hyaluronic acid composition, and photoinitiator described herein above or otherwise contemplated herein, resulting in covalent linkage of the functionalized hyaluronic acid molecules to the thiolated devitalized tissue particles. A quantity of the hydrogel precursor composition is deposited into the implant site, and the deposited hydrogel precursor composition is irradiated with a crosslink-activating wavelength, thereby causing crosslinking of the functionalized hyaluronic acid molecules within the deposited hydrogel precursor composition to form a crosslinked hydrogel implant in the implant site.

Certain non-limiting embodiments of the present disclosure are directed to a hydrogel implant that comprises a hydrogel precursor composition that has been implanted into an implant site in vivo and exposed to a crosslink-activating wavelength, thereby forming a crosslinked hydrogel. The hydrogel precursor composition comprises thiolated devitalized tissue particles, functionalized hyaluronic acid molecules, and photoinitiator as described herein above or otherwise contemplated herein, and wherein the functionalized hyaluronic acid molecules are crosslinked via covalent linkages to the thiolated devitalized tissue particles upon exposure of the hydrogel precursor composition to the crosslink-activating wavelength.

Any thiolated devitalized tissue particles known in the art or otherwise contemplated herein may be utilized in accordance with the present disclosure. Non-limiting examples thereof include thiolated devitalized cartilage (TDVC) particles, thiolated devitalized tendon (TDVT) particles, thiolated devitalized meniscus (TDVM) particles, thiolated demineralized bone matrix (TDBM) particles, as well as combinations thereof.

In at least certain non-limiting embodiments, the average molecular weight of the HA (or salts thereof) used in the hydrogels of the present disclosure is within a range of from about 3 kDa to about 20,000 kDa, or more particularly (but not by way of limitation) within a range of from about 5 kDa to about 5,000 kDa, and more particularly (but not by way of limitation) within a range of from about 500 kDa to about 2,000 kDa.

The hyaluronic acid can be functionalized via addition of one or more side groups at any position along the glycosaminoglycan chain and via any methods known in the art or otherwise contemplated herein. Particular side groups that can be utilized for functionalization of hyaluronic acid, along with methods of attachment of such side groups to hyaluronic acid, are well known in the art. One non-limiting example of side groups that can be utilized in accordance with the present disclosure are pentenoate functional groups.

In certain non-limiting embodiments, the hyaluronic acid has been functionalized to contain multiple 4-pentenoate side groups, thereby forming a pentenoate functionalized hyaluronic acid (PHA) which can be combined with thiolated tissue particles to thereby form the paste-like hydrogel precursor material. The hydrogel precursor composition exhibits a fluid yield stress for surgical placement in the pre-crosslinked form, and adequate compressive elastic modulus after crosslinking for material retention. The hydrogel precursor composition may further optionally comprise a photoinitiator for initiating and accelerating the crosslinking process and may further optionally comprise a dithiol crosslinking agent to increase hydrogel crosslinking.

In certain non-limiting embodiments, the hydrogel precursor composition has a compressive elastic modulus value exceeding about 2000 Pa. In a particular (but non-limiting) embodiment, the compressive elastic modulus value exceeds about 5000 Pa. In another particular (but non-limiting) embodiment, the compressive elastic modulus value is at least about 10 kPa.

In certain non-limiting embodiments, the hydrogel precursor composition has a fluid yield stress value in a range of from about 100 Pa to about 5000 Pa. In a particular (but non-limiting) embodiment, the fluid yield stress value is in a range of from about 100 Pa to about 2000 Pa. The fluid yield stress of the hydrogel precursor composition enables a user such as (but not limited to) a surgeon or other medical professional to place the material into an implant site (e.g., a defect site) without the composition leaking from the implant site. Once placed, the medical professional can irradiate the hydrogel precursor composition with a light wavelength which effects curing (crosslinking) to form the crosslinked hydrogel, which causes the tissue particles to be retained at the implant site as explained elsewhere herein. In order to facilitate such implantation and in situ curing or crosslinking, the hydrogel precursor has rheological properties of a paste-like material that can be placed into an implant site and remain in place without substantially contracting or shrinking in size before, during, or after curing or crosslinking.

In certain non-limiting embodiments, the hydrogel precursor composition may also include bioactive agents, such as (but not limited to) nucleic acid, nucleic acid complexes, polypeptides, proteins, small molecules, and/or traditional drugs as well as other substances for enhancing osteogenesis, chondrogenesis, and/or cell migration at or to the implant site. Non-limiting examples of bioactive agents may include growth factors, such as (but not limited to) cartilage and bone growth factors, or other tissue growth factors.

The tissue particles used in the compositions described herein can be of any size or size range which is effective in producing hydrogel precursor compositions and crosslinked hydrogel compositions which function in accordance with the present disclosure. Non-limiting particle sizes can be, for example, in a range of from about 20 nm to 105 µm.

In certain non-limiting embodiments, devitalized cartilage particles can be obtained by obtaining cartilage; mixing the cartilage with dry ice; grinding the mixture of dry ice and cartilage to obtain ground cartilage; and removing the dry ice from the ground cartilage. The process may also include cryogrinding the ground cartilage with a freezer mill; filtering the cryoground cartilage with a sieve to remove large particulates; and lyophilizing the ground cartilage to obtain a dry powder. Size exclusion filtering, such as (but not limited to) with a filter or sieve having apertures with the desired size, can be used to select particle sizes, and series of such filtering can be used to separate different particles sizes from each other. For example, the first filter can allow passage of any particles less than 300 µm, then the next filter can block particles larger than 200 µm (e.g., to collect particles 200-300 µm), then the next filter can block particles larger than 100 µm (e.g., to collect particles 100-200 µm), then the next filter can block particles larger than 50 µm (e.g., to collect particles 50-100 µm), then the next filter can block particles larger than 25 µm (e.g., to collect particles 25-50 µm), then the next filter can block particles larger than 10 µm (e.g., to collect particles 10-25 µm), then the next filter can block particles larger than 5 µm (e.g., to collect particles 5-10 µm), and then the next filter can block particles larger than 1 µm (e.g., to collect particles 1-5 µm). However, any of these ranges may be collected or omitted from the cartilage particles used in the formation of the hydrogel precursors and hydrogels. Non-limiting examples of specific sieve sizes used for filtering can be 45 µm and 105 µm, so as to collect particles larger, smaller, and therebetween.

The size exclusion filtering may also be done in the nanometer range, such as (but not limited to) the first filter can allow passage of any particles less than 300 nm, then the next filter can block particles larger than 200 nm (e.g., to collect particles 200-300 nm), then the next filter can block particles larger than 100 nm (e.g., to collect particles 100-200 nm), then the next filter can block particles larger than 50 nm (e.g., to collect particles 50-100 nm), and then the next filter can block particles larger than 25 nm (e.g., to collect particles 25-50 nm).

The precursor hydrogel composition can be applied to the implant site using any suitable manner known in the art or otherwise contemplated herein. In one embodiment, the hydrogel precursor composition can be applied using a spatula or other applicator tool, such as (but not limited to) a syringe or cannula. In one embodiment, the hydrogel precursor composition is mixed and stored under refrigeration for later use. In another embodiment, the hydrogel precursor composition is loaded into an applicator syringe and stored under refrigeration for later use. In another embodiment, the hydrogel precursor composition is mixed and handled for immediate use (e.g., within 2 hours). In certain non-limiting embodiments, the components of the kit are stored in separate compartments of a multi-compartment (multi-chamber) mixing syringe, wherein when a plunger is pushed, the tissue particle component and the hyaluronic acid component are mixed to form the hydrogel precursor composition, which can then be applied to the implant site (or stored for later use). The photoinitiator (and/or dithiol crosslinking agent) can be in a separate compartment in the syringe, or can be premixed with one or both of the tissue particle component and the hyaluronic acid component in the separate compartments. In another embodiment, the tissue particle component and the hyaluronic acid component are premixed together in one compartment (optionally with the dithiol crosslinking agent), and the photoinitiator is in a separate compartment. In certain non-limiting embodiments, the syringe contains a dry tissue particle component and a dry hyaluronic acid component mixture in one compartment and a saline solution in a separate compartment, which are then combined when the plunger is caused to combine the two separate compartments. Any suitable syringe known in the art can be used for application and/or mixing of the hydrogel precursor composition. Non-limiting examples of such mixing syringes are disclosed in U.S. Patent Application Publication Nos. 2003/0040701, 2004/0236273, 2005/0039669, 2005/0177100, 2007/0185440, 2010/0228121, 2011/0092906, 2014/0005610, 2015/0320935, 2015/0343153, 2016/0175537, 2016/0206818, and 2016/0106928.

In certain non-limiting embodiments, the tissue particle component comprises from about 5 wt % to about 30 wt % of the hydrogel precursor composition, and the hyaluronic acid component comprises from about 1 wt % to about 10 wt % of the hydrogel precursor composition. The photoinitiator component comprises from about 0.001 wt % to about 1 wt % of the hydrogel precursor composition, with the balance substantially made up of an aqueous solvent such as (but not limited to) phosphate-buffered saline (PBS) solution (e.g., about 60 wt % to about 94 wt %).

As noted above, in certain non-limiting embodiments, a dithiol crosslinking agent, such as (but not limited to) dithiothreitol (DTT), dithioerythritol (DTE), dithiobutylamine (DTBA), or poly(ethylene glycol) dithiol, can optionally also be added to the hydrogel precursor composition. The dithiol crosslinking agent may be present at any concentration that allows the agent to function as described herein; for example (but not by way of limitation), the dithiol crosslinking agent may be present in an amount in a range of from about 0.01 wt % to about 2.5 wt %.

In one non-limiting embodiment, the hydrogel precursor composition can comprise about 4 wt % PHA, about 10 wt % tissue particles, and about 86% PBS.

EXAMPLES

Certain non-limiting embodiments of the present disclosure will now be discussed in terms of several specific, non-limiting, examples. The examples described below will serve to illustrate the general practice of the present disclosure, it being understood that the particulars shown are merely exemplary for purposes of illustrative discussion of particular embodiments of the present disclosure only and are not intended to be limiting of the claims of the present disclosure.

Example 1

In certain non-limiting embodiments, the present disclosure is directed to new hydrogel precursor compositions and new hydrogel compositions based on functionalized tissue particles and functionalized hyaluronic acid. In at least one non-limiting embodiment, a hydrogel precursor composition comprises: (1) chemically modified hyaluronic acid molecules which have been functionalized with 4-pentenoate groups, thus forming 4-pentenoate functionalized hyaluronic acid (PHA); and (2) devitalized tissue particles having amine groups which have been functionalized with thiol (sulfhydryl) groups, thus forming thiol functionalized tissue particles. The hydrogel precursor can then be exposed to a light wavelength, such as (but not limited to) a UV wavelength, which causes the thiol groups on the tissue particles to react with the pentenoate groups on the PHA, thereby forming covalent thioether bonds between the tissue particles and the hyaluronic acid molecules to form a crosslinked hydrogel material in accordance with the present disclosure.

Any wavelength may be utilized, so long as exposure of the hydrogel precursor to the wavelength causes the thiol groups on the tissue particles to react with the pentenoate groups on the PHA and thus form covalent thioether bonds between the tissue particles and the hyaluronic acid molecules to form a crosslinked hydrogel material in accordance with the present disclosure. Non-limiting examples of wavelengths that can be utilized in accordance with the present disclosure include UV wavelengths in a range of from about 250 nm to about 400 nm.

Figure 2:
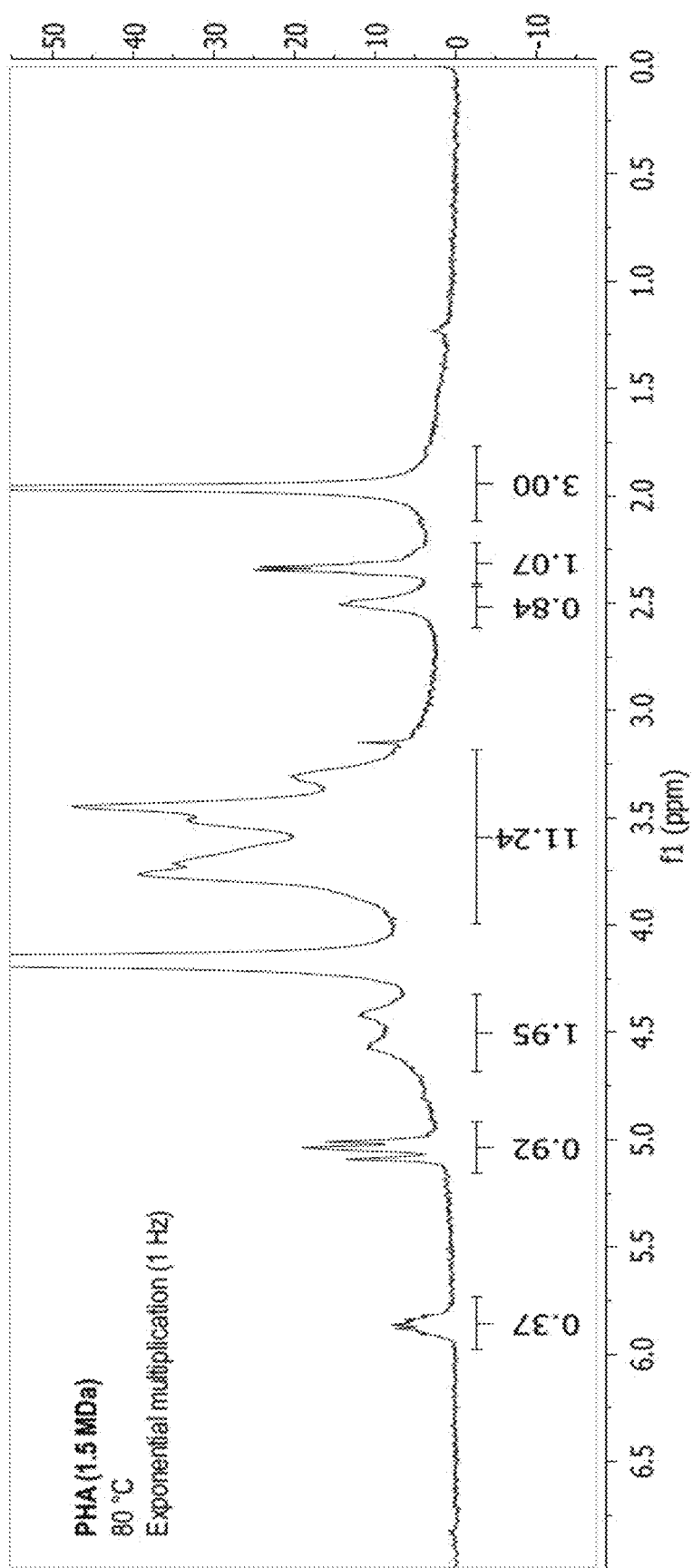
FIG. 2 is a Nuclear Magnetic Resonance (NMR) spectrograph of PHA formed by the reaction in FIG. 1 and showing a functionalization percentage of 37%, thus confirming the PHA reaction.

In the present non-limiting example, the PHA used in the compositions, kits, and methods of the present disclosure was made by reacting the hyaluronan polymer with 4-pentenoic anhydride following Protocol 1 presented below and schematically represented in FIG. 1. Functionalization of hyaluronic acid with 4-pentenoate groups was confirmed using nuclear magnetic resonance (NMR), as shown in FIG. 2. In alternate embodiments, the hyaluronic acid can be functionalized using, for example (but not by way of limitation), glycidyl methacrylate or 5-norbornene-2-carboxylic acid.

Protocol 1. Synthesis of Pentenoate Functionalized Hyaluronic Acid (PHA)

(1) For every 1.0 g of sodium hyaluronate (1.5 MDa, Lifecore Biomedical, MN), fully dissolve in 150 mL of DI water and stir at room temperature in the fume hood.

(2) For every gram of sodium hyaluronate dissolved, slowly add 100 mL of dimethylformamide (DMF) into the solution, allowing time to fully mix.

(3) For every gram of sodium hyaluronate dissolved, add 250 mg of 4-(dimethylamino)pyridine and allow to fully dissolve.

(4) Once the solution is fully mixed, set up a pH probe to constantly measure the pH of the solution. Adjust the pH to 9.5 using 0.5 M NaOH. Note: Have a pipette and stock of 0.5 M NaOH (~200 mL) solution ready before proceeding.

(5) For every gram of sodium hyaluronate, add 2.4 mL of 4-pentenoic anhydride; the pH will begin to change as soon as added.

(6) Maintain the pH between 8-9 for the duration of about 4 hours or until pH remains constant.

(7) Once pH change has ceased, add 5 g of NaCl for every gram of sodium hyaluronate being functionalized.

(8) The 4-pentenoate functionalized hyaluronic acid (PHA) can now be precipitated by adding 5 times the reaction volume of acetone. Centrifuge the liquid and discard the supernatant, retaining the pellet.

(9) Dissolve the PHA pellet in as little water as possible (~50 mL). Transfer the dissolved PHA to dialysis tubing and dialyze with DI water for 48 hours. Exchange dialysis DI water every 12 hours.

(10) The dialyzed PHA solution can now be frozen and lyophilized for later use.

Figure 3:
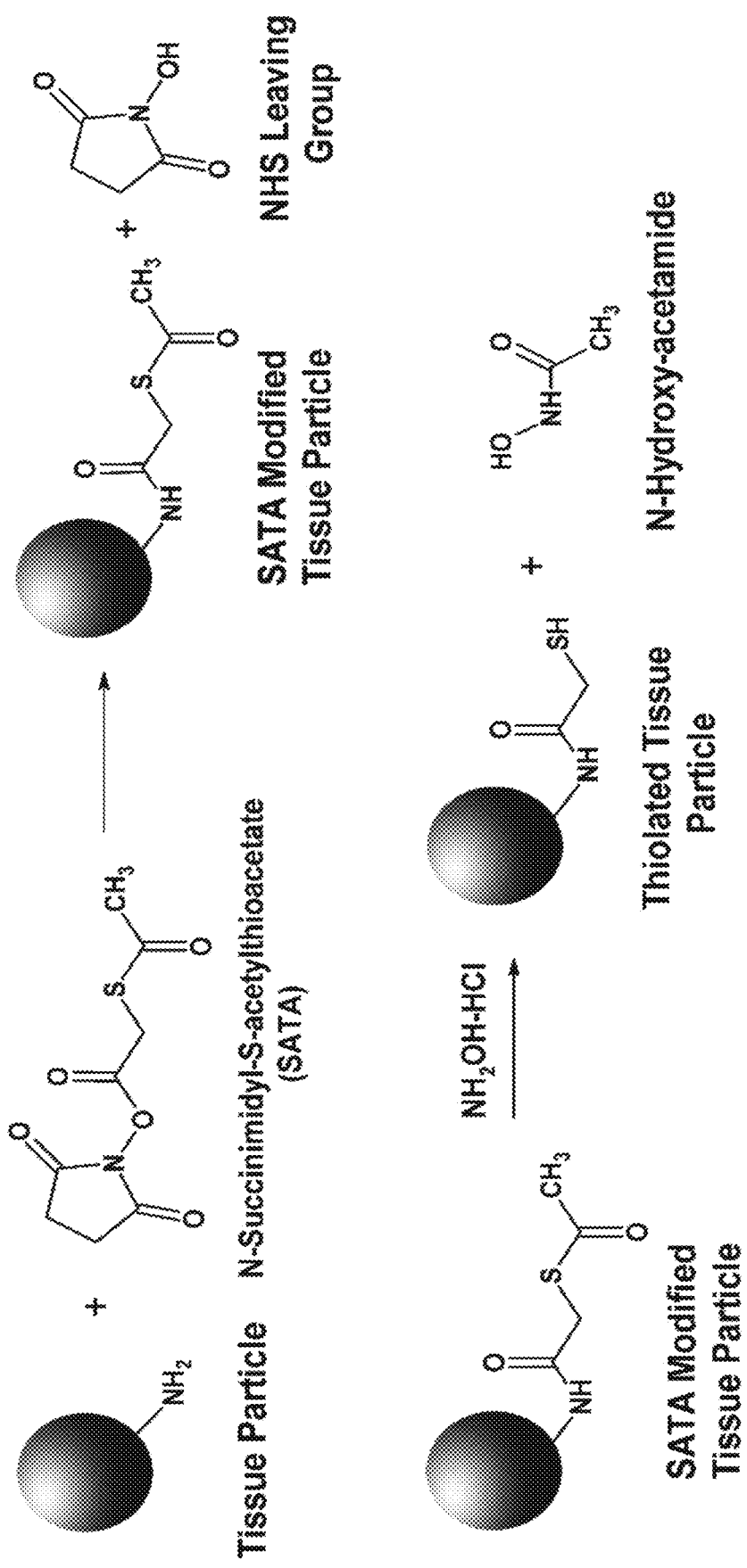
FIG. 3 shows the reaction of N-Succinimidyl-S-acetylthioacetate (SATA) with free amines on a tissue particle to form a SATA-modified tissue particle (upper reaction), and the reaction of the SATA-modified tissue particle with hydroxylamine-hydrochloride to form a thiolated tissue particle with a deprotected sulfhydryl group (lower reaction).
Figure 4:
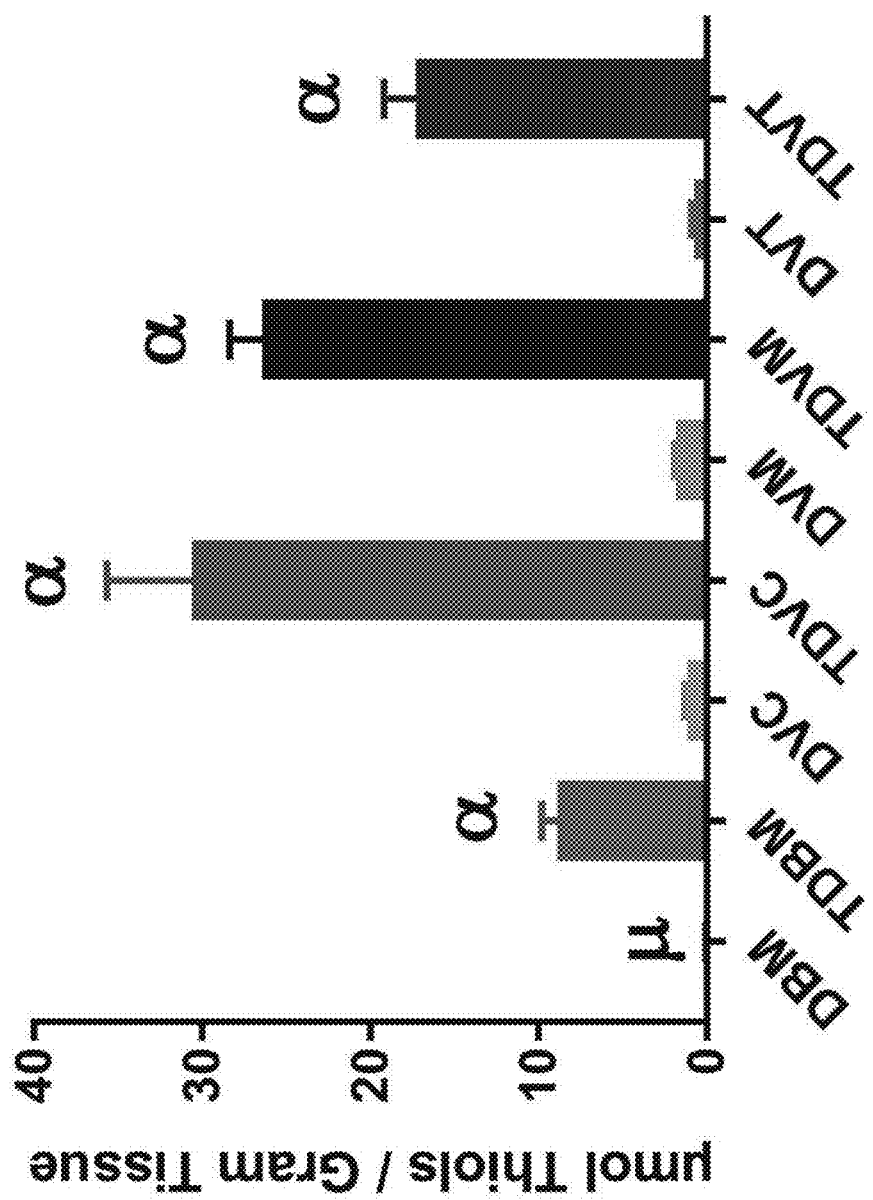
FIG. 4 is a graph showing confirmation of the thiolation of demineralized bone matrix (DBM) to form thiolated demineralized bone matrix (TDBM), thiolation of devitalized cartilage (DVC) to form thiolated devitalized cartilage (TDVC), thiolation of devitalized meniscus (DVM) to form thiolated devitalized meniscus (TDVM), and thiolation of devitalized tendon (DVT) to form thiolated devitalized meniscus (TDVT). Tissue particle thiolation was confirmed using an Ellman's assay. $\mu$=Value too small to appear on the graph. $\alpha$=Significant value compared to the non-thiolated version ($p<0.05$).

In a second step, cartilage, demineralized bone matrix (DBM), meniscus, or tendon tissues were cryoground into micron-sized particles and thiolated following Protocol 2 below. In the present non-limiting example, free amines on the surface of the tissue particles can be functionalized using N-Succinimidyl-S-acetylthioacetate (SATA) to create SATA-modified particles, which are then reacted with hydroxylamine-hydrochloride to deprotect the sulfhydryl group, resulting in thiolated tissue particles (FIG. 3). Addition of sulfhydryl groups to the various types of devitalized particles (cartilage, meniscus, tendon) was confirmed using an Ellman's assay (FIG. 4). Modification of tissue particles with SATA leads to a stable intermediate (providing a product with a longer shelf life).

Protocol 2: Synthesis of Thiolated-Tissue Particles (1) Dissolve tissue particles at a concentration of 5 mg/mL in Dissolving Solution (50 mM Sodium Phosphate (Cat #342483, Sigma-Aldrich, St. Louis, Mo.), 1 mM EDTA (Cat #17892, Thermo Fisher Scientific, Inc., Waltham, Mass.), pH 7.5).

(2) Dissolve N-succinimidyl S-acetylthioacetate (SATA) in DMF at a concentration of 15 mg/mL.

(3) Add 1.5 mL of SATA solution for every 100 mL of tissue solution.

(4) React for 1 hour at room temperature.

(5) Remove buffer using a Buchner funnel and Whatman 1 filter paper. Re-dissolve particles in fresh dissolving solution using the same volume of dissolving solution used in step 1.

(6) De-protect acetylated-SH groups by adding 10 mL of de-protecting solution for every 100 mL of dissolving solution. Deprotecting Solution: 0.5 M Hydroxylamine Hydrochloride (Cat #159417, Sigma-Aldrich, St. Louis, Mo.); 50 mM Sodium Phosphate; 25 mM EDTA, pH 7.5; React for 2 hours at room temperature.

(7) Dialyze for 48 hours in deionized water, perform exchanges every 12 hours.

(8) Freeze and lyophilize.

(9) Store long term at −20° C.

In alternate embodiments, instead of using SATA, the tissue particles can be thiolated using, for example (but not by way of limitation), N-succinimidyl S-acetylthiopropionate (SATP), Traut's reagent (2-iminothiolane), N-succinimidyl 3-(2-pyridyldithio) propionate (SPDP), Succinimidyloxycarbonyl-α-methyl-α-(2-pyridyldithio) toluene (SMPT), Citiolone (N-acetyl homocysteine thiolactone), S-Acetylmercaptosuccinic anhydride, or γ-Thiobutyrolactone (4-Butyrothiolactone).

Figure 5:
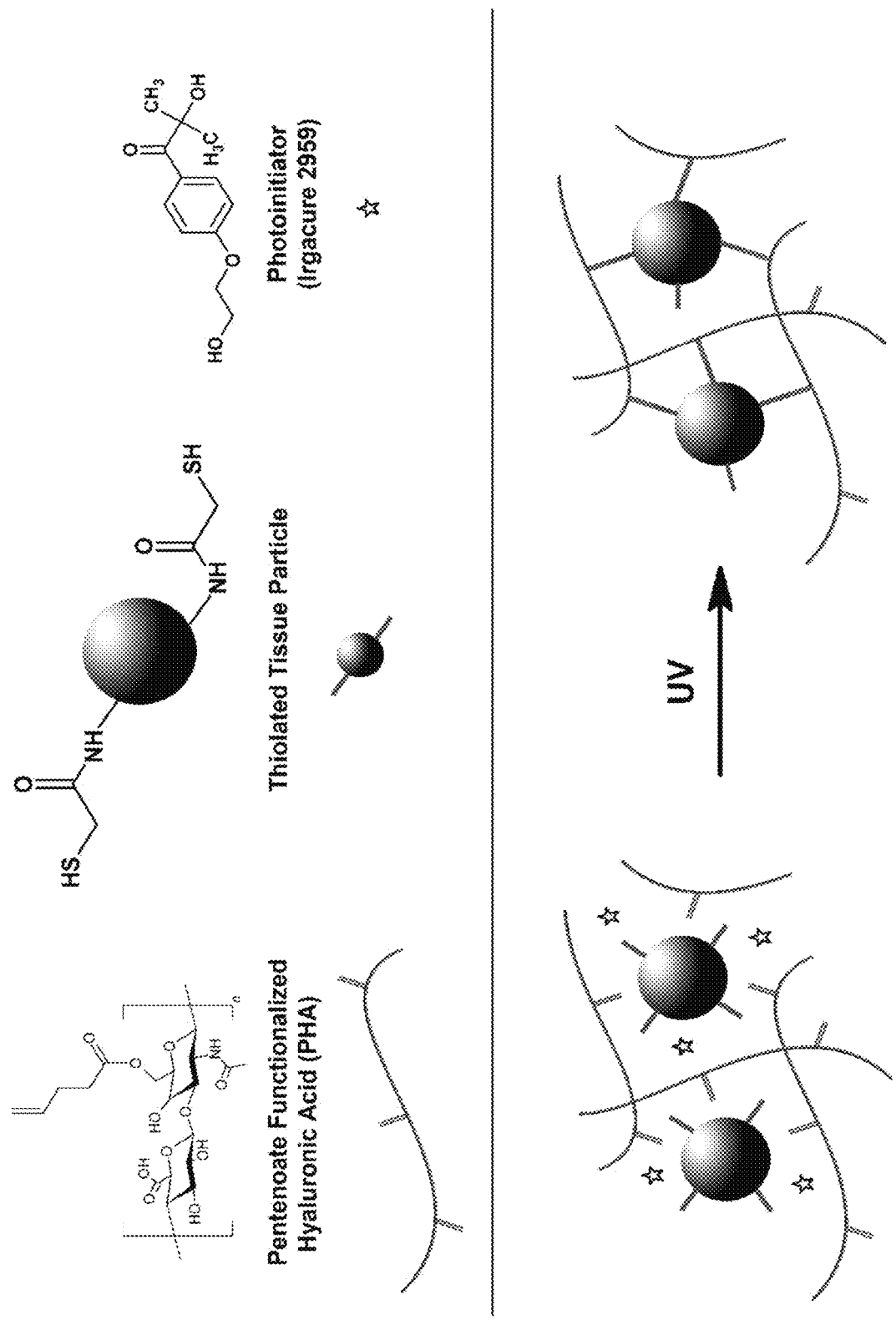
FIG. 5 shows a reaction scheme for one embodiment of photo-crosslinking tissue particle hydrogel synthesis in accordance with the present disclosure. Thiolated tissue particles are combined with pentenoate functionalized hyaluronic acid (PHA) and a photoinitiator (e.g., 12959) in solution. The mixture is irradiated with an appropriate UV-light wavelength, thereby causing the photoinitiator to catalyze the covalent bonding between the free sulfhydryl groups of the thiolated tissue particles and the alkene groups of the PHA. The bonding creates a hydrogel comprised of a covalently bound interconnected HA network.

The PHA and thiolated tissue particles can then be combined with a photoinitiator to create a paste-like hydrogel precursor composition for physical placement into a defect site. After deposition into the defect site, the material is exposed to an appropriate light wavelength, such as (but not limited to) a UV wavelength, thereby causing cross-linkage of the hyaluronic acid molecules via thioether bonds with the tissue particles to form a static material (FIG. 5). Non-limiting examples of photoinitiators that can be used in accordance with the present disclosure include 2-Hydroxy-4'-(2-hydroxyethoxy)-2-methylpropiophenone (IRGACURE®-2959 or 12959, Ciba Specialty Chemicals, Tarrytown, N.Y.) and LAP (Lithium Phenyl(2,4,6-trimethylbenzoyl)phosphinate). Numerous other photoinitiators are known in the art that can be used in the present compositions, kits, and methods, and as such, the use of any other photoinitiators known in the art or otherwise contemplated herein also falls within the scope of the present disclosure.

Example 2

Tissue hydrogels made according to the procedures in Example 1 can be used and evaluated in an in vivo rat calvarial defect model. Extracellular matrix (ECM) from sources other than bone can be used to promote comparable bone regeneration in a critical size calvarial defect model. A non-limiting embodiment of an experimental protocol is described below.

Preparation of Devitalized Tissue

Cartilage, meniscus, and tendon tissues are harvested from the knees of 10 castrated male Berkshire hogs (7-8 months of age, 120 kg) purchased from an abattoir. Tissue devitalization occurs as follows. Harvested tissues are rinsed, strained, and chopped into small pieces. Tissues are coarse ground using a cryogenic tissue grinder (e.g., BioSpec Products, Bartlesville, Okla.), then frozen and lyophilized. Tissues are then cryoground using a freezer-mill (e.g., SPEX 6775, SamplePrep, Metuchen, N.J.). Devitalized cartilage (DVC), devitalized meniscus (DVM), and devitalized tendon (DVT) are stored at −20° C. for later use. Further examples and details of a devitalization process that can be used in accordance with the present disclosure are shown in U.S. Patent Application Publication No. 2017/0065742.

Synthesis of Pentenoate Functionalized Hyaluronic Acid (PHA)

In a non-limiting embodiment, pentenoate functionalized hyaluronic acid (PHA) is synthesized by dissolving hyaluronic acid (HA, Mw=1.01-1.8 MDa, e.g., Lifecore Biomedical, Chaska, Minn.) in DI water at a concentration of 0.5% (w/v). Once fully dissolved, DMF is slowly added to the solution to achieve a final ratio of 3:2 (water:DMF). The pH of the solution is then adjusted to 9.5 using NaOH. Pentenoic anhydride (e.g., Cat #471801, Sigma-Aldrich, St. Louis, Mo.) is then added in 5 M excess relative to HA, and the pH is maintained between 8-9 for approximately 4 hours. Afterwards, NaCl is added to the solution to achieve a final concentration of 0.5 M. The PHA is then precipitated in 4 volumes of acetone and centrifuged at 7,000×g to separate the PHA from solution. PHA pellets are then dissolved in DI water and transferred to dialysis packets (e.g., MWCO 6000). PHA is dialyzed against DI water for 48 hours, performing DI water exchanges every 12 hours. After dialysis, the PHA solution is frozen and lyophilized. Dry PHA is stored at −20° C. for later use.

Hydrogel Precursor Preparation

PHA and tissue particles are weighed dry and combined then dispersed in PBS solution containing 0.05% 2-Hydroxy-4'-(2-hydroxyethoxy)-2-methylpropiophenone as a photoinitiator (e.g., 12959, Cat #410896) and 1% dithiothreitol (DTT, e.g., Cat # D0632, Sigma-Aldrich, St. Louis, Mo.). Dry material combinations are sterilized using ethylene oxide gas (AN74i, Anderson Anprolene, Haw River, N.C.), and the PBS-I2959-DTT solution is sterile-filtered prior to use in vivo. Hydrogel precursor solutions are allowed to reach ambient conditions for 2 h before implanting.

Rheological Testing of Hydrogel Precursor

Hydrogel precursor fluid yield stress can be determined using an AR2000 controlled stress rheometer (e.g., TA-Instruments, New Castle, Del.). Measurements are performed using a 20-mm diameter crosshatched stainless steel plate geometry and a crosshatched Peltier plate cover at 37° C. and a gap distance of 500 µm (n=3). The Peltier solvent trap is used to ensure no material dehydration during testing. An oscillatory shear stress sweep from 1-8000 Pa is used to measure hydrogel precursor fluid yield stress. Material fluid yield stress is determined by the cross-over point of the storage (G') and loss modulus (G").

Mechanical Testing of Crosslinked Hydrogel

Crosslinked hydrogel compressive elastic modulus is determined using, e.g., an RSA III dynamic mechanical analyzer (TA-Instruments). Hydrogels are prepared for testing using the method described in Beck E C, Lohman B L, Tabakh D B, Kieweg S L, Gehrke S H, Berkland C J, et al. ("Enabling Surgical Placement of Hydrogels Through Achieving Paste-Like Rheological Behavior in Hydrogel Precursor Solutions." (2015) *Ann Biomed Eng.*, 43(10): 2569-76). Briefly, hydrogel precursor solutions are loaded into 2-mm thick Teflon molds that are sandwiched between glass microscope slides and secured using clamps. Hydrogels are then crosslinked using a 312 nm UV-light at 9 mW/cm$^2$ for 2 minutes (e.g., EB-160C, Spectroline, Westbury, N.Y.). Post-crosslinking, circular hydrogels are cut using a sterile 3 mm punch and swelled in PBS for 24 hours before proceeding with mechanical testing. Swollen hydrogels are measured using a stereo microscope and micrometer to determine the diameter, and hydrogel height is measured using the RSA III. Hydrogels are compressed at a constant rate of 0.005 mm/s until 30% strain. The compressive elastic modulus is calculated from the linear portion slope of the stress-strain curve between 5-15% strain.

Animal Model and Surgical Method

Male Sprague-Dawley rats are used at an age of 7-8 weeks; surgeries are conducted between 8-9 weeks of age. The calvaria is exposed by creating an incision on the posterior periphery of the skull to pull back the skin and periosteum. Using a dental trephine, a critical size 7.5 mm diameter defect is created on the center of the calvaria. The circular piece of calvarial bone is carefully removed, leaving the dura matter intact. Approximately 50 µL of hydrogel solution is then syringed into the space and smoothed/shaped to the defect using a sterile spatula. PHA hydrogel is then crosslinked using a handheld 312 nm UV-light in animals treated with a PHA hydrogel. The skin and periosteum are then carefully draped over the defect site and sutured in place. The sham group receives the same surgical method without the addition of material, the DBX® groups receive approximately 50 µL of DBX® (Demineralized Bone Matrix) Putty (Depuy Synthes, West Chester, Pa.), and the uninjured group receives no surgical intervention. Calvarial bone is harvested 8 weeks after post-implantation.

Micro-Computed Tomography (µCT)

In one non-limiting embodiment, micro-computed Tomography is performed using, e.g., a Quantum FX imaging system (PerkinElmer, Waltham, Mass.) with a 50-kV X-ray source at 160 µA. µCT imaging is conducted on harvested rat calvarial bone 8 weeks post-implantation. µCt scans are analyzed using, e.g., Avizo computational software (FEI Company, Hillsboro, Oreg.) to quantify regenerated bone volume. Regenerated bone is confirmed using peripheral bone as the threshold. Orange coloring indicates newly formed bone within the original 7.5 mm defect. Regenerated bone is presented as a percentage (%) within the 7.5 mm diameter defect, where total bone was determined using uninjured rat calvarial bone.

Histology and Immunohistochemistry (IHC)

After fixing in 10% phosphate-buffered formalin for 48 hours and µCT imaging, explanted cranial bone samples are submerged in 70% ethanol for long term storage. Embedding, sectioning, and staining of tissue is performed. Briefly, cranial bone is sectioned in the sagittal plane and embedded in paraffin wax following a standard protocol. Paraffin blocks are cut to a thickness of 4 µm and affixed to glass microscope slides. The Hematoxylin and eosin (H&E) staining system is performed, e.g., using a Leica ST5020 multistainer (Leica Biosystems, Wetzlar, Germany).

In Vitro Cell Culture and Experimental Design

Pre-osteoblast mouse calvarial cells (e.g., MC3T3-E1, ATCC, Manassas, Va.) are cultured in minimum essential medium-α (e.g., Cat #12561072, Thermo Fisher Scientific, Waltham, Mass.) supplemented with 10% fetal bovine serum (FBS, e.g., Cat #16000044, Thermo Fisher Scientific) and 1% penicillin/streptomycin (e.g., Cat #15140-122, Thermo Fisher Scientific). Medium is exchanged every other day, and cells are cultured until a passage number of 2 before use in the current study. Statistically significant experimental groups from the 8-week in vivo study are chosen to be refined in vitro to determine the minimum tissue particle concentration to achieve a desirable cellular response. Following the results of the in vivo study, PHA, PHA-tissue particle groups can be selected to refine the tissue particle concentration. Approximately 50 µL of material is injected by syringe into each well of a 96-well plate, centrifuged at 1000×g for 5 minutes to evenly coat the bottom of the well, then crosslinked using the handheld UV light for 2 minutes. MC3T3-E1 cells are seeded at a concentration of $10^4$ cells per well (150 µL volume) directly on top of the crosslinked material in each well of the 96-well plate and allowed to flourish for 10 days.

Biochemical Assays

During the 10-day cell culture experiment, bi-daily media sampling is conducted to assess the concentration of secreted osteocalcin (OCN) using an ELISA kit (e.g., Cat # LS-F12227, LifeSpan BioSciences, Seattle, Wash.) according to the manufacturer's guidelines. After 2 and 10 days of cell culture, cells are lysed with 200 µL, of lysis buffer (e.g., Cat # R1060-1-50, Zymo Research, Irvine, Calif.), and DNA content is determined using, e.g., the Quant-iT™ PicoGreen™ assay (Cat # P7589, Thermo Fisher Scientific, Waltham, Mass.) according to the manufacturer's guidelines. Hydrogels without MC3T3 cells serve as controls for the study. Hydrogel constructs are then dissolved in 100 µL, of 1M hydrochloric acid to determine the amount of deposited calcium. Calcium is assayed using, e.g., the QuantiChrom™ calcium assay kit (BioAssay Systems, Hayward, Calif.) according to the manufacturer's instructions.

Statistical Methods

GraphPad Prism software (Graphpad Software Inc, La Jolla, Calif.) can be used to conduct statistical analyses. A one-way analysis of variance with groups of factors is used for analyzing mechanical testing and µCT, and a two-way analysis of variance with groups of factors is used to analyze biochemical assays. Tukey's post-hoc analysis is used to compare between groups. Fluid yield stress testing can use n=3 samples per group. Compressive elastic modulus, µCT, PicoGreen, osteocalcin ELISA, and calcium testing can use n=5 samples per group; all data is reported as the mean±the standard deviation.

While the present disclosure has been described herein in connection with certain embodiments so that aspects thereof may be more fully understood and appreciated, it is not intended that the present disclosure be limited to these particular embodiments. On the contrary, it is intended that all alternatives, modifications, and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein, or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicant reserves the right to amend, add to, or replace the claims indicated herein below in subsequent patent applications.

What is claimed is:

1. An implantable hydrogel precursor composition, comprising:
   a devitalized tissue particle composition comprising thiolated devitalized tissue particles;
   a hyaluronic acid composition comprising functionalized hyaluronic acid molecules; and
   a photoinitiator for initiating covalent linkage of the functionalized hyaluronic acid molecules to the thiolated devitalized tissue particles; and
   wherein the devitalized tissue particle composition, the hyaluronic acid composition, and the photoinitiator form a hydrogel precursor composition when combined, and wherein the hydrogel precursor composition is capable of forming a crosslinked hydrogel when exposed to a crosslink-activating wavelength.

2. The implantable hydrogel precursor composition of claim 1, wherein the functionalized hyaluronic acid molecules comprise pentenoate functional groups.

3. The implantable hydrogel precursor composition of claim 1, further comprising a dithiol crosslinking agent.

4. The implantable hydrogel precursor composition of claim 1, wherein the thiolated devitalized tissue particles of the devitalized tissue particle composition are selected from the group consisting of thiolated devitalized cartilage particles, thiolated devitalized tendon particles, thiolated devitalized meniscus particles, thiolated demineralized bone particles, and combinations thereof.

5. The implantable hydrogel precursor composition of claim 1, wherein the hydrogel precursor composition has a fluid yield stress in a range of from about 100 Pa to about 5000 Pa.

6. The implantable hydrogel precursor composition of claim 1, wherein the crosslinked hydrogel has a compressive elastic modulus exceeding about 2000 Pa.

7. A kit for use in repair or regeneration of a damaged tissue, the kit comprising:
   one or more containers comprising:
      a devitalized tissue particle composition comprising thiolated devitalized tissue particles;
      a hyaluronic acid composition comprising functionalized hyaluronic acid molecules; and
      a photoinitiator for initiating covalent linkage of the functionalized hyaluronic acid molecules to the thiolated devitalized tissue particles; and
   wherein when combined, the devitalized tissue particle composition, the hyaluronic acid composition, and the photoinitiator form a hydrogel precursor composition, and wherein the hydrogel precursor composition is capable of forming a crosslinked hydrogel when exposed to a crosslink-activating wavelength.

8. The kit of claim 7, wherein the functionalized hyaluronic acid molecules comprise pentenoate functional groups.

9. The kit of claim 7, wherein the one or more containers further comprises a dithiol crosslinking agent.

10. The kit of claim 7, wherein the thiolated devitalized tissue particles of the devitalized tissue particle composition are selected from the group consisting of thiolated devitalized cartilage particles, thiolated devitalized tendon particles, thiolated devitalized meniscus particles, thiolated demineralized bone particles, and combinations thereof.

11. The kit of claim 7, further comprising instructions for using the kit to form the hydrogel precursor composition and treating the hydrogel precursor composition to form the crosslinked hydrogel.

12. The kit of claim 7, wherein the hydrogel precursor composition has a fluid yield stress in a range of from about 100 Pa to about 2000 Pa.

13. The kit of claim 7, wherein the crosslinked hydrogel has a compressive elastic modulus exceeding about 5000 Pa.

14. A method of forming a hydrogel implant in an implant site in vivo, the method comprising the steps of:
   forming a hydrogel precursor composition by combining:
      (1) a devitalized tissue particle composition comprising thiolated devitalized tissue particles;
      (2) a hyaluronic acid composition comprising functionalized hyaluronic acid molecules; and
      (3) a photoinitiator for initiating covalent linkage of the functionalized hyaluronic acid molecules to the thiolated devitalized tissue particles to cause crosslinking of the functionalized hyaluronic acid molecules;
   depositing a quantity of the hydrogel precursor composition into the implant site; and
   irradiating the deposited hydrogel precursor composition with a crosslink-activating wavelength causing crosslinking of the functionalized hyaluronic acid molecules within the deposited hydrogel precursor composition to form a crosslinked hydrogel implant in the implant site.

15. The method of claim 14, wherein the implant site is selected from the group consisting of bone defects, tendon defects, cartilage defects, and meniscus defects.

16. The method of claim 14, wherein the functionalized hyaluronic acid molecules comprise pentenoate functional groups.

17. The method of claim 14, wherein the hydrogel precursor composition comprises a dithiol crosslinking agent.

18. The method of claim 14, wherein the thiolated devitalized tissue particles of the devitalized tissue particle composition are selected from the group consisting of thiolated devitalized cartilage particles, thiolated devitalized tendon particles, thiolated devitalized meniscus particles, thiolated demineralized bone particles, and combinations thereof.

19. The method of claim 14, wherein the hydrogel precursor composition has a fluid yield stress in a range of from about 100 Pa to about 5000 Pa.

20. The method of claim 14, wherein the crosslinked hydrogel implant has a compressive elastic modulus exceeding about 2000 Pa.

21. A hydrogel implant, comprising:
   a hydrogel precursor composition that has been implanted into an implant site in vivo and exposed to a crosslink-activating wavelength, thereby forming a crosslinked hydrogel, the hydrogel precursor composition comprising thiolated devitalized tissue particles, functionalized hyaluronic acid molecules, and a photoinitiator, wherein the functionalized hyaluronic acid molecules are crosslinked via covalent linkages to the thiolated devitalized tissue particles upon exposure of the hydrogel precursor composition to the crosslink-activating wavelength.

22. The hydrogel implant of claim 21, wherein the functionalized hyaluronic acid molecules comprise pentenoate functional groups.

23. The hydrogel implant of claim 21, wherein the hydrogel precursor composition comprises a dithiol crosslinking agent.

24. The hydrogel implant of claim 21, wherein the thiolated devitalized tissue particles are selected from the group consisting of thiolated devitalized cartilage particles, thiolated devitalized tendon particles, thiolated devitalized meniscus particles, thiolated demineralized bone particles, and combinations thereof.

25. The hydrogel implant of claim 21, wherein the implant site is selected from the group consisting of bone defects, tendon defects, cartilage defects, and meniscus defects.

26. The hydrogel implant of claim 21, wherein the hydrogel precursor composition has a fluid yield stress in a range of from about 100 Pa to about 5000 Pa.

27. The hydrogel implant of claim 21, wherein the crosslinked hydrogel has a compressive elastic modulus exceeding about 2000 Pa.

28. The implantable hydrogel precursor composition of claim 1 or 2, further comprising a dithiol crosslinking agent.

29. The implantable hydrogel precursor composition of any one of claims 1-3, wherein the thiolated devitalized tissue particles of the devitalized tissue particle composition are selected from the group consisting of thiolated devitalized cartilage particles, thiolated devitalized tendon particles, thiolated devitalized meniscus particles, thiolated demineralized bone particles, and combinations thereof.

30. The implantable hydrogel precursor composition of any one of claims 1-4, wherein the hydrogel precursor composition has a fluid yield stress in a range of from about 100 Pa to about 5000 Pa.

31. The implantable hydrogel precursor composition of any one of claims 1-5, wherein the crosslinked hydrogel has a compressive elastic modulus exceeding about 2000 Pa.

32. The kit of claim 7 or 8, wherein the one or more containers further comprises a dithiol crosslinking agent.

33. The kit of any one of claims 7-9, wherein the thiolated devitalized tissue particles of the devitalized tissue particle composition are selected from the group consisting of thiolated devitalized cartilage particles, thiolated devitalized tendon particles, thiolated devitalized meniscus particles, thiolated demineralized bone particles, and combinations thereof.

34. The kit of any one of claims 7-10, further comprising instructions for using the kit to form the hydrogel precursor composition and treating the hydrogel precursor composition to form the crosslinked hydrogel.

35. The kit of any one of claims 7-11, wherein the hydrogel precursor composition has a fluid yield stress in a range of from about 100 Pa to about 2000 Pa.

36. The kit of any one of claims 7-12, wherein the crosslinked hydrogel has a compressive elastic modulus exceeding about 5000 Pa.

37. The method of claim 14 or 15, wherein the functionalized hyaluronic acid molecules comprise pentenoate functional groups.

38. The method of any one of claims 14-16, wherein the hydrogel precursor composition comprises a dithiol crosslinking agent.

39. The method of any one of claims 14-17, wherein the thiolated devitalized tissue particles of the devitalized tissue particle composition are selected from the group consisting of thiolated devitalized cartilage particles, thiolated devitalized tendon particles, thiolated devitalized meniscus particles, thiolated demineralized bone particles, and combinations thereof.

40. The method of any one of claims 14-18, wherein the hydrogel precursor composition has a fluid yield stress in a range of from about 100 Pa to about 5000 Pa.

41. The method of any one of claims 14-19, wherein the crosslinked hydrogel implant has a compressive elastic modulus exceeding about 2000 Pa.

42. The hydrogel implant of claim 21 or 22, wherein the hydrogel precursor composition comprises a dithiol crosslinking agent.

43. The hydrogel implant of any one of claims 21-23, wherein the thiolated devitalized tissue particles are selected from the group consisting of thiolated devitalized cartilage particles, thiolated devitalized tendon particles, thiolated devitalized meniscus particles, thiolated demineralized bone particles, and combinations thereof.

44. The hydrogel implant of any one of claims 21-24, wherein the implant site is selected from the group consisting of bone defects, tendon defects, cartilage defects, and meniscus defects.

45. The hydrogel implant of any one of claims 21-25, wherein the hydrogel precursor composition has a fluid yield stress in a range of from about 100 Pa to about 5000 Pa.

46. The hydrogel implant of any one of claims 21-26, wherein the crosslinked hydrogel has a compressive elastic modulus exceeding about 2000 Pa.

* * * * *

UNITED STATES PATENT AND TRADEMARK OFFICE
CERTIFICATE OF CORRECTION

PATENT NO. : 10,744,229 B1
APPLICATION NO. : 16/330237
DATED : August 18, 2020
INVENTOR(S) : Jakob M. Townsend and Michael S. Detamore Page 1 of 1

It is certified that error appears in the above-identified patent and that said Letters Patent is hereby corrected as shown below:

On the Title Page

Under Abstract "46 Claims, 5 Drawing Sheets" should read -- 27 Claims, 5 Drawing Sheets --.

In the Specification

Column 2, Line 42: Delete "12959)" and replace with -- I2959) --.

Column 12, Line 39: Delete "(-200mL)" and replace with -- (~200mL) --.

Column 12, Line 52: Delete "(-50mL)." and replace with -- (~50mL). --.

Column 13, Line 50: Delete "12359," and replace with -- I2959, --.

Column 14, Line 41: Delete "(e.g., 12359," and replace with -- (e.g., I2959, --.

In the Claims

Column 19, Lines 16-45: Delete Claims 28-34 in their entirety.

Column 20, Line 1-44: Delete Claims 35-46 in their entirety.

Signed and Sealed this
Fifth Day of January, 2021

Andrei Iancu
*Director of the United States Patent and Trademark Office*